(12) United States Patent
De Lucca, II et al.

(10) Patent No.: US 6,310,091 B1
(45) Date of Patent: Oct. 30, 2001

(54) FUNGICIDAL SAPONIN, CAY-1, AND ISOLATION THEREOF FROM CAPSIUM SPECIES FRUIT

(75) Inventors: Anthony J. De Lucca, II, Metairie; John M. Bland, Slidell; Craig B. Vigo, Metairie, all of LA (US); Claude P. Selitrennikoff, Denver, CO (US)

(73) Assignees: The United States of America as represented by the Secretary of Agriculture, Washington, DC (US); Mycologics, Inc., Denver, CO (US)

( * ) Notice: Subject to any disclaimer, the term of this patent is extended or adjusted under 35 U.S.C. 154(b) by 0 days.

(21) Appl. No.: 09/661,757

(22) Filed: Sep. 14, 2000

(51) Int. Cl.[7] .................. A61K 31/34; A61K 31/343; C07D 311/96; C07D 407/04
(52) U.S. Cl. .................. 514/462; 514/468; 514/451; 514/452; 549/343; 549/344
(58) Field of Search .................. 549/343, 344; 514/462, 468, 451, 452

(56) References Cited
U.S. PATENT DOCUMENTS 6,063,381    5/2000    Staggs .

OTHER PUBLICATIONS

Yajima Mizuo et al, English Abstract Caplus 134:83456, Isolation and Structure of antimicrobial . . RN#318277–23–5 . . . Jun. 2000.*

Oxford Dictionary of Biochemistry and Molecular Biology Revised edition 2000, p. 418.*

* cited by examiner

Primary Examiner—Alan L. Rotman
Assistant Examiner—Rita Desai
(74) Attorney, Agent, or Firm—M. Howard Silverstein; Joseph A. Lipovsky; John D. Fado

(57) ABSTRACT

A novel antifungal compound, "CAY-1", was isolated from the dried fruit of *Capsicum frutescens* (cayenne pepper), purified to homogeneity, and characterized as a novel sterol glycoside (a saponin) with a molecular mass of 1243.35 Da. CAY-1 demonstrates antifungal activity against a large variety of fungal organisms associated with diseases in plants, animals and humans including, but not limited to, *Aspergillus flavus*, *A. fumigatus*, *A. parasiticus*, *A. niger*, *Pneumocystis carnii* and *Candida albicans*, but has minimal toxic effects on mammalian cells.

15 Claims, 9 Drawing Sheets

CAY-1

$C_{57}H_{94}O_{29}$

MW=1243.35

CAY-1

$C_{57}H_{94}O_{29}$

MW=1243.35

CAY-1 effect on *Aspergillus flavus* viability

CAY-1 Effect on *Aspergillus fumigatus* Viability

The effect of CAY-1 on the viability of *Aspergillus parasiticus*

CAY-1 effect on *Aspergillus niger* viability

CAY-1 Effect on HeLa Cells

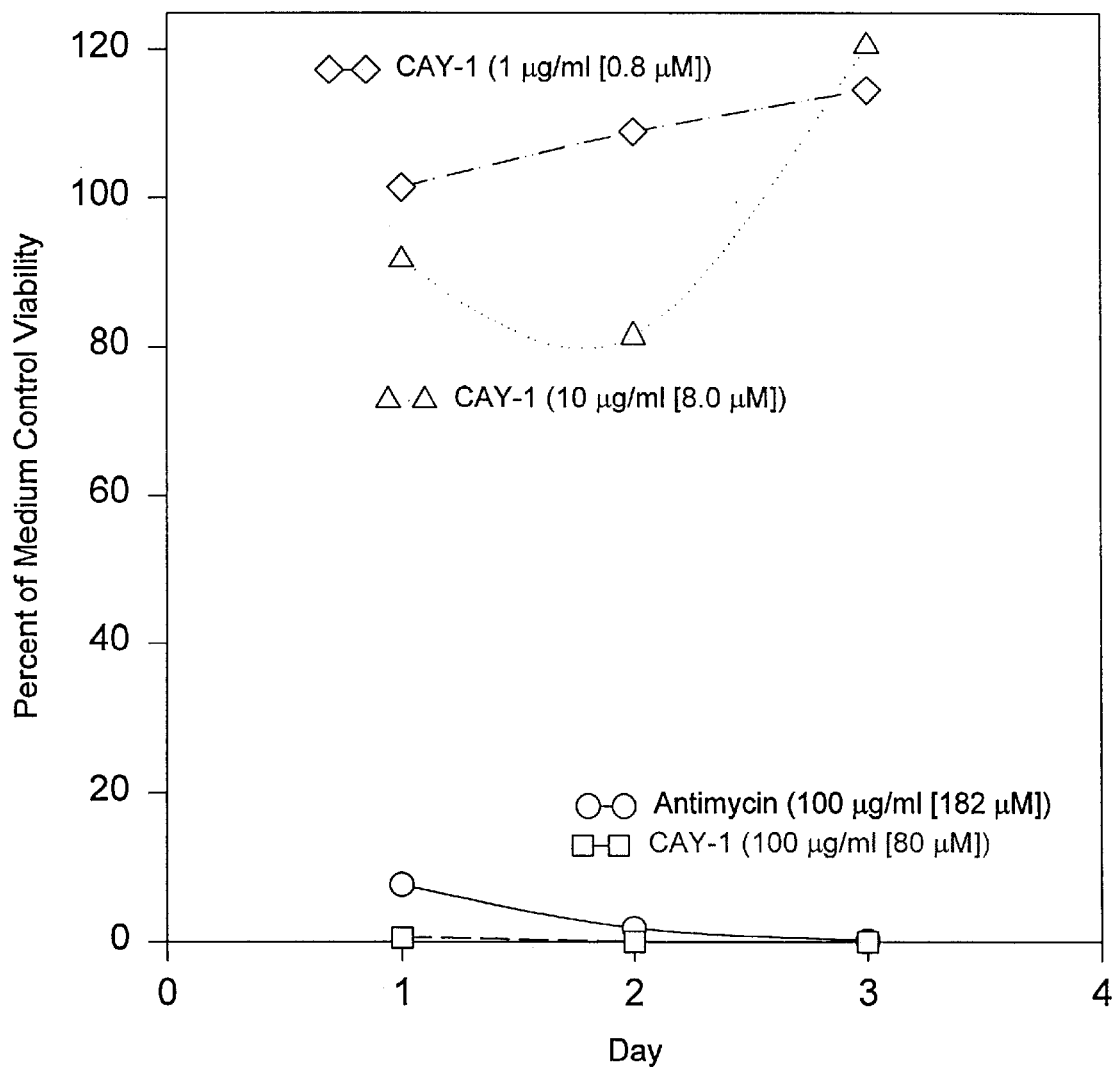

FUNGICIDAL SAPONIN, CAY-1, AND ISOLATION THEREOF FROM CAPSIUM SPECIES FRUIT

BACKGROUND OF THE INVENTION

1. Field of the Invention

This invention relates to a novel fungicidal saponin and its isolation from cayenne pepper or other capsicum species fruit. This compound shows potential for improving crop resistance to a variety of aflatoxin-producing fungi and also as a pharmaceutical against human and animal fungal-induced diseases.

2. Description of the Prior Art

The identification of novel antifungal agents has been a continuing challenge. Due to the occurrence of new disease epidemics in agricultural crops and as a result of the growing resistance to antimicrobial drugs, there is an ongoing search for new antifungal compounds having unique structures.

The need for novel antifungal agents is significant, and is especially critical in the medical field. Immunocompromised patients provide perhaps the greatest challenge to modern health care delivery. During the last three decades there has been a dramatic increase in the frequency of fungal infections in these patients (Herbrecht, R., *Eur. J. Haematol.*, 1996, 56:12–17; Cox, G. et al., *Curr. Opin. Infect. Dis.*, 1993, 6:422–426; Fox, J. L., *ASM News*, 1993, 59:515–518). Deep-seated mycoses are increasingly observed in patients undergoing organ transplants and in patients receiving aggressive cancer chemotherapy (Alexander, B. D. et al., *Drugs*, 1997, 54:657–678). The most common pathogens associated with invasive fungal infections are the opportunistic yeast, *Candida albicans*, and the filamentous fungus, *Aspergillus fumigatus* (Bow, E. J., *Br. J. Haematol.*, 1998, 101:1–4; Warnock, D. W., *J. Antimicrob. Chemother.*, 1998, 41:95–105). There are an estimated 200,000 patients per year who acquire nosocomial fungal infections (Beck-Sague, C. M. et al., *J. Infect. Dis.*, 1993, 167:1247–1251); bloodstream fungal infections have a mean mortality rate of 55 w. Also adding to the increase in the numbers of fungal infections is the emergence of Acquired Immunodeficiency Syndrom (AIDS) where virtually all patients become affected with some form of mycoses (Alexander, B. D. et al., *Drugs*, 1997, 54:657–678; *HIV/AIDS Surveillance Report*, 1996, 7(2), Year-End Edition; Hood, S. et al., *J. Antimicrob. Chemother.*, 1996, 37:71–85). The most common organisms encountered in these patients are *Cryptococcus neoformans*, *Pneumocystis carinii*, and *C. albicans* (*HIV/AIDS Surveillance Report*, 1996, 7(2), Year-End Edition; Polis, M. A. et al., *AIDS: Biology, Diagnosis, Treatment and Prevention*, fourth edition, 1997). New opportunistic fungal pathogens such as *Penicillium marneffei*, *C. krusei*, *C. glabrata*, *Histoplasma capsulatum*, and *Coccidioides immitis* (*HIV/AIDS Surveillance Report*, 1996, 7(2), Year-End Edition; Ampel, N. M., *Emerging Infectious Diseases*, 1996, 2:109–116) are also being reported with regularity in immunocompromised patients throughout the world.

Currently available drugs for the treatment of fungal infections include amphotericin B (a macrolide polyene), which interacts with fungal membrane sterols, flucytosine (a fluoropyrimidine), which interferes with fungal protein and DNA biosynthesis, and a variety of azoles (e.g. ketoconazole, itraconazole, and fluconazole) that inhibit fungal membrane-sterol biosynthesis (Alexander, B. D. et al., *Drugs*, 1997, 54:657–678). Even though amphotericin B has a broad range of activity and is viewed as the "gold standard" of antifungal therapy, its use is limited due to infusion-related reactions and nephrotoxicity (Alexander, B. D. et al., *Drugs*, 1997, 54:657–678; Warnock, D. W., *J. Antimicrob. Chemother.*, 1998, 41:95–105). Flucytosine usage is also limited due to the development of resistance and its narrow spectrum of activity. The widespread use of azoles is causing the emergence of clinically-resistant strains of Candida spp. (Alexander, B. D. et al., *Drugs*, 1997, 54:657–678; Boschman, C. R. et al., *Antimicrob. Agents Chemother.*, 1998, 42:734–738). Although advances in the formulation of amphotericin B have decreased its nephrotoxicity (Graybill, J. R., *Clin. Infect. Dis.*, 1996, 22(Suppl. 2):S166–S178) and new classes of agents are in various stages of clinical development, the impact of fungal infections in the clinical management of patients underscores the clear need for new antifungals.

Historically, the screening of soil microorganisms and extracts obtained from terrestrial plants and animals has yielded novel natural products which themselves, or through chemical modification and synthesis, have been a rich source of bioactive agents for the treatment of plant, animal and human diseases (Gullo, V. P., *The discovery of natural products with therapeutic potential*, Butterworth-Heinemann, Boston, 1994; Shu, Y.-Z., *J. Nat. Prod.*, 1998, 61:1053–1071). A review of the 520 newly-approved drugs reported between 1983 and 1994 indicates that 157 (30%) are unmodified natural products or semi-synthetic analogs (Cragg, G. M. et al., *J. Nat. Prod.*, 1997, 60:52–60).

The screening of natural sources such as microbial fermentations and plant extracts has led to the discovery of many clinically useful drugs that play a major role not only in the treatment of microbial infections, but also in the treatment of many human and plant diseases. The increasing clinical importance of emerging pathogens as well as drug-resistant fungi has lent additional urgency to identify novel, active compounds. The most promising lead antifungal compounds are those derived from natural products. The lipopeptides are potent broad-spectrum antifungal agents that inhibit the synthesis of the fungal cell-wall polymer, (Gullo, V. P., *The discovery of natural products with therapeutic potential*, Butterworth-Heinemann, Boston, 1994; Cragg, G. M. et al., *J. Nat. Prod.*, 1997, 60:52–60) β-D-glucan (Denning, D. W., *J. Antimicrob. Chemother.*, 1997, 40:611–614). The pradimicins are a group of benzonaphthacene quinones which posses a broad spectrum of activity and bind to the mannoproteins of the fungal cell membrane (Oki, T. et al., *J. Antibiot.*, 1998, 41:1701–1704). The sordarins are tetracyclic diterpene glycosides, which have a broad spectrum of antifungal activity and inhibit the elongation step of fungal protein synthesis (*Drugs Future*, 1997, 22:1221–1225).

Another class of antifungal agents are the saponins, which are glycosides consisting of one or more sugars linked to a steroid or triterpene core. They are noted for their detergent properties and some have been found to be microbicidal. Some are antiviral (Sindambiwe, J. B. et al., *J. Nat. Prod.*, 1998; 61:585–590; Simões, C. M. O. et al., *Planta. Med.*, 1990, 56:652–653; Simões, C. M. O. et al., *Phytother. Res.*, 1999, 13:323–328) and appear to inhibit viral DNA and capsid protein syntheses (Simões, C. M. O. et al., *Phytother. Res.*, 1999, 13:323–328), while others have antifungal properties. Extracts of *Eriocephalus africanus L.*, *Felicia erigeroides* DC, and *Helichrysum crispum* (L.) D. Don, inhibited *Candida albicans* growth (Salie, F. et al., *J. Ethanopharmacol.*, 1996, 52:27–33). Saponins from the tubers of *Cyclamen coum* Miller inhibited the growth of several Candida species and *Cryptococcus neoformans* (Calis, I. et al., *Planta. Med.*, 1997, 63:166–170). Triterpenoid *saponins* have been shown to exhibit a wide spectrum of activity against yeast as well as the dermatophytes, *Trichophyton rubrum* and *T. mentagrophytes* (Favel, A. et al., *Planta. Med.*, 1994, 60:50–53). Recently, a jujubogenin saponin isolated from *Colubrina retusa*, a rhamnaceous plant growing in Venezuela (Li, X. C. et al., *J. Nat. Prod.*, 1999, 62:672–677), was shown to be moderately effective against *C. albicans, Cryptococcus neoformans*, and *A. fumigatus* (MICs, 50 µg/ml). Oats contain two families of saponins, the triterpenoid avenacins and the steroidal avenacosides (Osborn, A. E. et al., *The Plant Cell*, 1996, 8:1821–1831).

Fenugreek produces a steroid saponin and the corresponding aglycone that becomes inhibitory against fungi such as *Candida albicans* after treatment with β-glucosidase (Sauvaire, Y. et al., *Saponins Used in Foods and Agriculture*, Plenum Press, New York, 1996, pp. 37–46). Stems of *Colubrina retusa* contain several jujubogenin saponins with no to moderate antifungal properties. The most active compound showed growth inhibitory effects (MICs of ~50 µg/mL) against *C. albicans, Cryptococcus neoformans*, and *A. fumigatus* while the other two jujubogenins showed little or no activity (Li, X. et al., *J. Nat. Prod.*, 1999, 62:674–677). Another saponin family, the spirostanol sapogenins from the bulbs of leak (*Allium porrum*), are antifungal. Four of the eight members of this family inhibited *Fusarium culmorum* growth with $IC_{50}$ values of 30–35 µg/mL (Carotenuto, A. et al., *Phytochem.*, 1999, 51:1077–1082). The salzmannianosides are two saponins isolated from *Serjania salzmanniana* (Ekabo, O. et al., *J. Nat. Prod.*, 1996, 59:431–435) and displayed activity against *Candida albicans* and *Cryptococcus neoformans* at 16 and 8 µg/mL, respectively. Three triterpene saponins, cyclainorin, deglucocyclamin, and from *Cyclamen mirabile* and *Cyclamen coum* were shown to have inhibitory properties against a number of Candida species (CaliÔ, I. et al., *J. Nat. Prod.*, 1997, 60:315–31). Not all saponins have antifungal properties.

As described hereafter, our search for antifungal compounds from higher plant species has included investigation of the genus Capsicum. Capsicum is a member of the Solanaceae, a large tropical plant family (Eshbaugh, W. H., *New Crops*, Wiley, New York, 1993, pp. 132–139). However, only five species of peppers have been domesticated; *C. annuum, C. baccatum, C. chinense, C. frutescens*, and *C. pubescens*. They are noted for the pungency and medicinal properties of their fruit. *C. frutescens*, commonly known as cayenne pepper, is also used in the Tabasco® pepper products.

Peppers have been used for many centuries to inhibit food spoilage (Billing, J. et al., *Q. Rev. Biol.*, 1998, 73:2–47). For example, the Mayan pharmacopoeia describes the use of the tissues of certain Capsicum species in herbal remedies for a variety of ailments of microbial origin (Cichewicz, R. H. et al., *J. Ethanopharm.*, 1996, 52:61–70). To date, only a few bioactive compounds have been isolated from this pepper family. The most commonly-known compounds belong to the capsaicinoid group, of which capsaicin (n-vanillyl-8-methyl-6-(E)-nonamide) is the predominant species. Capsaicin has been studied extensively and has demonstrated a high degree of biological activity affecting nervous, cardiovascular, and digestible systems (Virus, R. M. et al., *Life Sci.*, 1979, 25:1273–1284; Monsereenusom et al., *CRC Critical Reviews in Toxicology*, 1982, 10:321–339; Surh, Y. J. et al., *Life Sci.*, 1995, 56:1845–1855). Presently, two prescription drugs are based on capsaicin. Zostrix® (Genderm) is used for the treatment of shingles and arthritis while Axsain® (GalenPharma) is used for relief of neuralgias, diabetic neuropathy, and postsurgical pain.

Most of the compounds isolated from this genus have been obtained from *C. annuum* (bell pepper). One such compound is a 75 amino-acid polypeptide named J1 (Meyer, B. et al., *Plant Physiol.*, 1996, 112:615–622) which acts as a fungistatic agent against *Fusarium oxysporum* and *Botrytis cinerea*. Bell pepper stems produce a 34 kDa β-1,3-glucanase, which has been shown to inhibit hyphal growth of *Phytophthora capsici* (Kim, Y. J. et al., *Physiol. Mol. Plant Pathol.*, 1997, 50:103–105) and to act synergistically with a pepper chitinase in inhibiting the growth of *F. oxysporum*.

*C. annuum* roots and seeds produce steroidal glycosides, named capsicosides A-D (Yahara, S. et al., *Phytochem.*, 1994, 37:831–835), having a wide range of biological properties such as froth formation, hemolytic activity, complexing with cholesterol, antitumor, antitussive, and platelet-aggregation inhibitory properties (Mimaki, Y. et al., *Saponins Used in Traditional and Modern Medicine*, Plenum Press, New York, 1996, pp. 101–110; Back, K. et al., *Plant Cell. Physiol.*, 1998, 39:899–904). To date, none of the Capsicum species has been identified as producing saponins with antifungal properties.

SUMMARY OF THE INVENTION

We have now identified a novel antifungal compound, from the dried fruit of *Capsicum frutescens* (cayenne pepper). This compound, referred to herein as "CAY-1", was purified to homogeneity and has been characterized as a novel sterol glycoside (a saponin) with a molecular mass of 1243.35 Da.

In accordance with this discovery, it is an object of the invention to introduce a new chemical compound in the family of saponins.

It is also an object of the invention to provide a novel compound having activity against a large variety of fungal organisms associated with diseases in plants, animals and humans.

A particular object of the invention is to provide a novel saponin that is lethal against aflatoxin-producing fungi, including *Aspergillus flavus, A. fumigatus, A. parasiticus* and *A. niger*.

Another particular object of the invention is to provide a novel saponin that inhibits human mycoses induced by fungal pathogens including *Pneumocystis carnii* and *Candida albicans*, but has minimal toxic effects on mammalian cells.

A further object of the invention is to provide an isolate of cayenne pepper as an important value-added agricultural product.

Other objects and advantages of the invention will become readily apparent from the ensuing description.

BRIEF DESCRIPTION OF THE DRAWINGS

FIG. 9 shows the effect of CAY-1 on A549 lung cells with time at various concentrations.

DETAILED DESCRIPTION OF THE INVENTION

CAY-1 Isolation.

As previously mentioned, the CAY-1 compound of the invention is isolated from cayenne pepper (*Capsicum frutescens*), a member of the Solanaceae. Typically, the dry pepper is first finely ground by any conventional means, such as in a pin mill, Wiley mill, or the like. The ground pepper is then extracted with a suitable solvent. We have found that 1% (w/v) potato dextrose broth (PDB) at pH of about 6.0 in a 1:4 pepper:PDB (w/v) ratio is especially effective for this purpose. The pepper/PDB slurry is preferably cooled to a temperature of 1–5° C. such as by placing it in ice for several hours in order to stabilize the antifungal agent against degradation by other plant components until the fractionation is commenced. Thereafter, the liquid fraction is separated from the solids and recovered. The separation may be effected by centrifugation with recovery and filtration of the supernatant. The fungicidal activity is eluted from the supernatant with an aqueous methanol or other polar solvent. The activity will elute from an extraction cartridge with 75% (v/v) MeOH. The active agent is then purified from the methanol eluate, such as by liquid chromatography, high performance liquid chromatography (HPLC), or the like.

Antifungal Activity.

Figure 1:
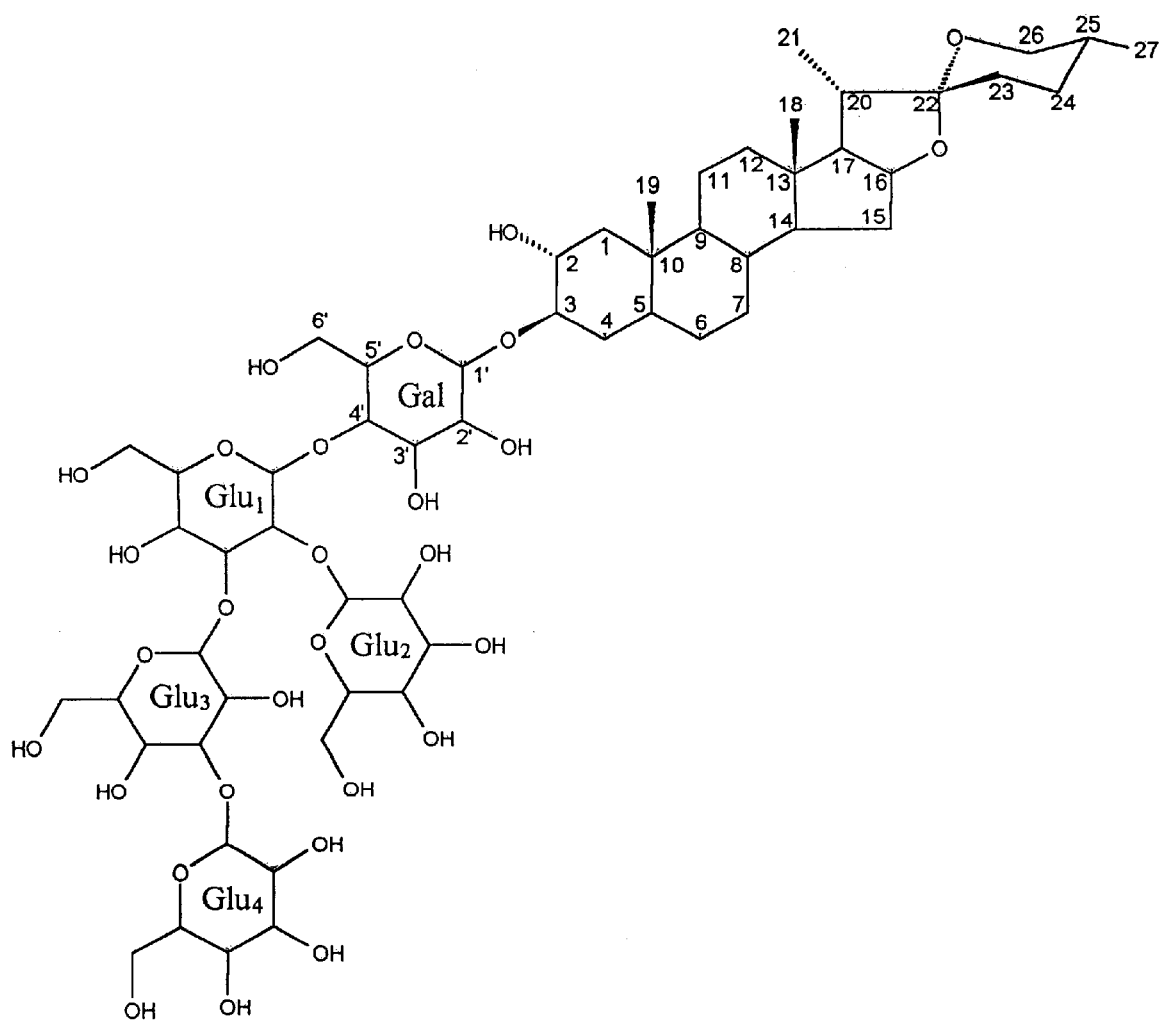
FIG. 1 shows the chemical structure of CAY-1.

CAY-1 is a novel steroidal saponin (mol. wt. 1243.35 Da.) having the structure shown in FIG. 1. This saponin is comprised of a sterol moiety to which is attached by an ester bond a glycoside having a galactose and 4 glucose molecules having β-linkages. It is useful for treating a wide variety of fungal infections in plants, humans and animals. The utility of CAY-1 in the treatment of infection caused by *Aspergillus flavus, A. fumigatus, A. parasiticus, A. niger, Pneumocystis carnii* and *Candida albicans* has been demonstrated in the Examples, below. Additionally, it is expected that CAY-1 would be useful for the treatment of infections caused by other fungal species, including, but not limited to Blastomyces, such as *B. dermatitidis*; Blastoschizomyces, such as *B. capitatus*, other species of Candida, such as *C. glabrata, C. krusei, C. pseudotropicalis*, and *C. tropicalis*; Cladosporium, such as *C. carrionii*; Coccidioides, such as *C. immitis*; Cryptococcus, such as *C. neoformans*; Geotrichum, such as *G. clavatum*; Histoplasma, such as *H. capsulatum*; Paracoccidioides, such as *P. brasiliensis*; Penicillium, such as *P. marneffei*; Scedosporium, such as *S. apiosperum*; Sporothrix, such as *S. schenckii*; and Trichosporon, such as *T. beigelii*.

Application and Administration.

The CAY-1 fungicidal saponin of the invention can be applied or administered by any conventional method to the locus of fungal infection or potential fungal infection. For agronomic applications, examples of such loci include, without limitation thereto, surfaces of plant foliage, flowers, seeds, fruits and vegetables, roots, tubers, and even the soil in the vicinity of seeds, plants, and the like. The CAY-1 could also be administered to plants systemically, as by injection or absorption into the tissues. For human and veterinary applications, the CAY-1 could be administered through various routes, including oral, nasal, rectal, parenteral, implant, topical, and the like.

Formulation.

The CAY-1 will typically be applied in a suitable solid or liquid carrier or vehicle that is compatible with the organism being treated.

Compositions containing CAY-1 intended for agronomic uses may be formulated as an aqueous spray or dip, wettable powder, drench, dust, granule, pellet, etc. Typical carriers used in such formulations would include without limitation, mineral earths, such as silicas, silica gels, silicates, talc, kaolin, limestone, lime, chalk, bole, loess, clay, dolomite, diatomaceous earth, calcium sulfate, magnesium sulfate, and magnesium oxide; organic materials, such as cereal hulls, shredded tree bark, wood chips, nutshells, and cellulose powders; and fertilizers, such as ammonium sulfate, ammonium phosphate, ammonium nitrate, ureas. The CAY-1 may be applied to the aforementioned solid carriers as a surface treatment (e.g. a spray), or may be blended therewith and shaped into granules or pellets. Formulations comprising CAY-1 may also include other adjuvants, such as wetting agents, sticking agents and the like. When used together with a liquid vehicle, the CAY-1 could either be dissolved or dispersed therein. CAY-1 may also be blended with other active ingredients, such as herbicides, insecticides, bactericides, nematocides, molluscicides, growth regulators, micronutrients, and the like.

For human and veterinary applications, the CAY-1 may be formulated with many of the same carriers and vehicles listed above. Pharmaceutically-acceptable carriers and excipients useful for administration of pharmaceuticals are well-known in the art. For instance, tablets and capsules intended for oral administration may contain binding agents, such as starch, gums, and polyhydroxy alcohols; fillers, such as sucrose, lactose, starch, sorbitol; disintegrants, such as potato starch or sodium starch glycollate; surfactants, such as sodium lauryl sulphate; suspension agents, emulsifiers, preservatives, flavorants, minerals, salts, effervescence agents, etc. CAY-1 can also be administered in deionized water, physiological saline, 5% (w/v) dextrose solution, vegetable oil, alcohol, propylene glycol or other liquid vehicle. Particular advantage of the antifungal properties of CAY-1 can be taken by incorporating the saponin into lotions, ointments, creams, eye, ear and nose drops, shampoos, body powders, pessaries, wound dressings, inhalers, sanitary devices, skin patches, sprays, aerosols, and so forth.

The selected carrier or vehicle would of course be consistent with the intended mode of application or administration of CAY-1. Typical modes of application for agronomic uses would include spraying, fogging, atomizing, dusting, broadcasting, coating, drenching, and the like. For medical and veterinary applications, modes of administration would include ingestion, parenteral injection (intramuscular, subcutaneous, intraperitoneal, and intravenous), topical dusting or spraying, and inhalation.

Effective Levels.

The expressions "an effective amount" and "a suppressive amount" are used herein in reference to that quantity of CAY-1 treatment which is necessary to obtain a reduction in the level of disease, as measured by fungal growth or the symptoms associated with fungal growth, relative to that occurring in an untreated control under suitable conditions of treatment as described herein. In cases where the saponin is applied prophylactically, use of these terms means that the disease is prevented at a significant level relative to untreated controls. It is implied that an effective amount of CAY-1 would be less than any amount that would induce significant detrimental side effects in the organism being treated for the fungal infection. This implication is reinforced by the use of the expression "pharmaceutically effective amount". The actual rate and amount of application will vary depending on the fungal organism being controlled, the point in its growth phase that treatment is commenced, the substrate being treated and other environmental factors. In the bioassays conducted on media as described in the Examples, below, CAY-1 was shown to be effective in vitro against the germinating conidia of several pathogenic Aspergillus species at application levels between about 3.0 and 20.0 µM (4–25 µg/ml). The novel saponin is also effective against *C. albicans* and *P. carinii* in vitro at levels as low as about 3 µM and 5 µM, respectively. Importantly, CAY-1 is not lethal to the mammalian cells tested in Example 3 at the concentrations shown to be effective against the aforementioned fungi and yeast. The time course study described in Example 2 indicates that CAY-1 rapidly reduces fungal viability at a dose dependent rate. The particular dose regimen will be dependent upon a plurality of factors, such as the species, size, sex and age of the individual being treated, the target fungal species, the severity of infection, the mode of administration, etc. Upon taking these factors into account, actual dose level and regimen could be readily determined by the person of ordinary skill in the art.

The following examples are intended only to further illustrate the invention and are not intended to limit the scope of the invention which is defined by the claims.

EXAMPLE 1

Extraction, Purification and Analysis of Fungicide from Pepper

Ground, dry commercial cayenne pepper was purchased and stored at 0° C. until needed. A 1% (w/v) solution of potato dextrose broth (PDB, Difco, Detroit, Mich.), used as an extraction buffer and bioassay medium, was prepared, adjusted to pH 6.0, and sterilized. The ground pepper was thoroughly mixed with PDB at a ratio of 1:5 (wt:vol) and placed in ice (~4° C.) for 5 hours. The pepper slurry was centrifuged for 10 min at 5,000×RCF (4° C.) and the supernatant removed. It was then centrifuged at 11,500× RCF for 4 min and the supernatant removed. The supernatant was then passed through a 0.45µ filter to remove any fines, and was stored at 0° C. until needed.

The crude extract was added onto a Waters polymeric Oasis® HLB Extraction cartridge (Milford, Mass.) and sequentially eluted with 3 ml of 0, 25, 50, 75, and 100% (v/v) methanol. The eluates were evaporated with $N_2$ and freeze dried. Fungicidal activity of each eluate was determined as described below in 1% (w/v) PDB and found only to occur in the 75% (w/v) methanol fraction. The fungicidal compound, CAY-1, was purified by further fractionating the 75% (w/v) methanol fraction which had been freeze dried and reconstituted in 1% (w/v) PDB on a Beckman® HPLC equipped with a reversed phase column. Since the active fraction was not detected by UV, the presence of the fungicide was determined by mass spectrometry (MS) and bioassays. The purity, structure, and molecular weight of the isolated compound was determined by MS and Nuclear Magnetic Resonance (NMR). NMR experimental techniques consisted of Total Correlation Spectroscopy (TOCSY), Heteronuclear Multiple-Quantum Coherence (HMQC), and Heteronuclear Multiple-Bond Correlation (HMBC). It was determined that CAY-1 is a steroidal saponin with a molecular weight of 1243.35 Da. The structure is given in FIG. 1. A galactose and four glucose sugars are linked by an ester bond to the number 3 carbon of the steroid as shown in the figure.

EXAMPLE 2

Bioassays

1. Filamentous fungi. Filamentous fungi used in bioassays included *Aspergillus flavus*, *A. fumigatus*, *A. niger*, *A. parasiticus* and *Fusarium oxysporum*. The fungicidal properties of CAY-1 for the nongerminated and germinating conidia of these fungi were determined separately as described by De Lucca et al. [*Med. Mycol.*, 36:291–298 (1998)] and De Lucca et al. [*Antimicrob. Agents Chemother.* 43:371–373 (1999)]. Bioassays were performed separately in RPMI-1640 broth with glutamine and 0.0165 M MOPS but without sodium bicarbonate (BioWhittaker, Walkersville, Md.) and 1% (w/v) PDB to determine whether different media would affect CAY-1 fungicidal properties. Two separate experiments were conducted in each medium (n=8 per medium).

A suspension of the aforementioned fungi were prepared separately in the appropriate medium. Conidia ($10^4$ conidia/ml) were used immediately for the nongerminated conidial assays while conidia ($10^5$ conidia/ml) were incubated for 7.5 hours at 30° C. to obtain germinating conidia. Serial dilutions of CAY-1 were prepared in the appropriate medium (totaling 225 µl) to which was added 25 µl of the conidial suspensions. The control consisted of 225 µl of medium and 25 µl of the conidial suspension. After mixing, the samples were incubated for 30 min (30° C.). Samples were then spread on potato dextrose agar plates which were incubated at 30° C. for 24 hours. Colonies were then enumerated.

Figure 2:
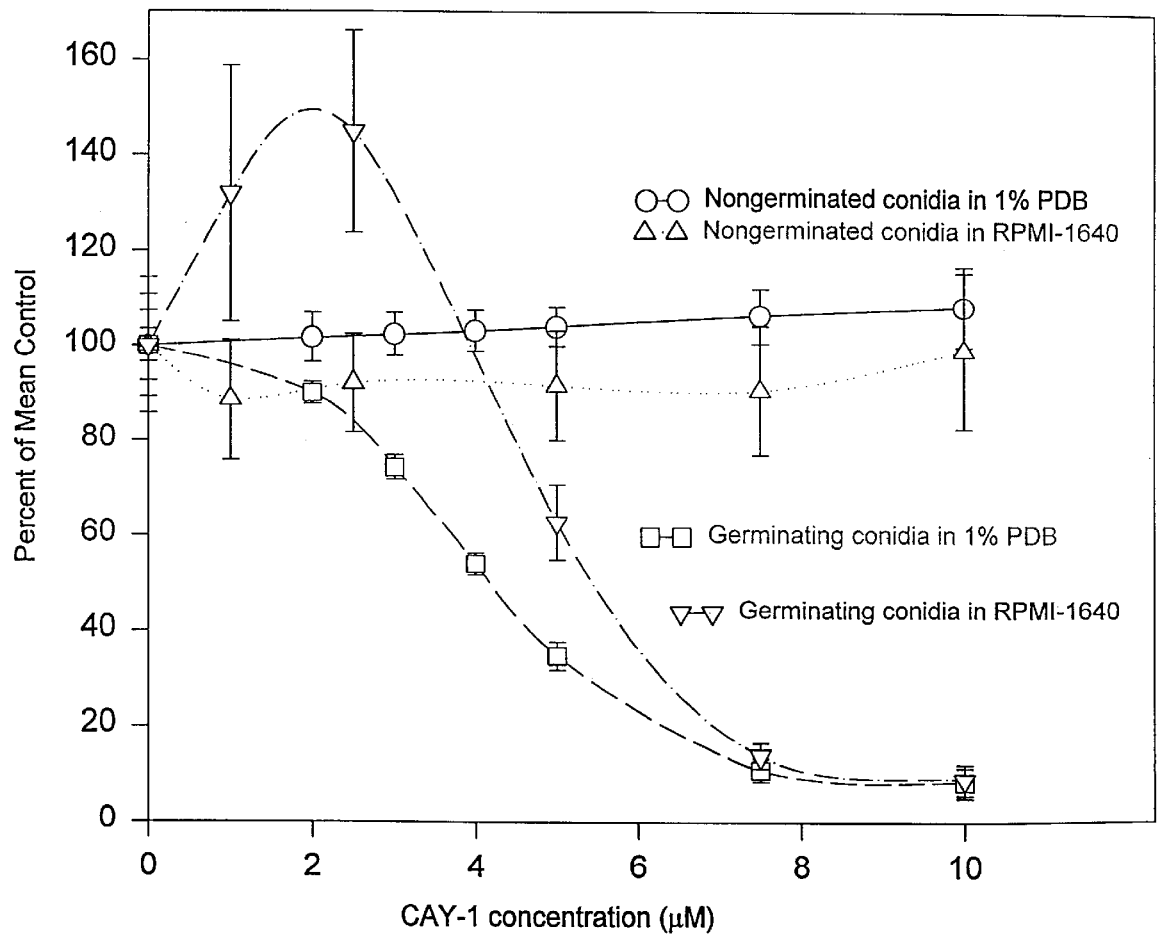
FIG. 2 shows the effect of CAY-1 on *Aspergillus flavus* as a function of CAY-1 concentration.

CAY-1 was fungicidal for the germinating conidia of the tested Aspergillus species with the degree of lethality being species dependent. CAY-1 was lethal to *A. flavus* in both 1% (w/v) PDB (p=0.0026) and RPMI-1640 (p=0.0187) at 7.5 µM (9.3 µg/ml) in both media (TABLE 1 & FIG. 2). The $LD_{95}$ for *A. flavus* was obtained at 12.5 µM (15.5 µg/ml).

Figure 3:
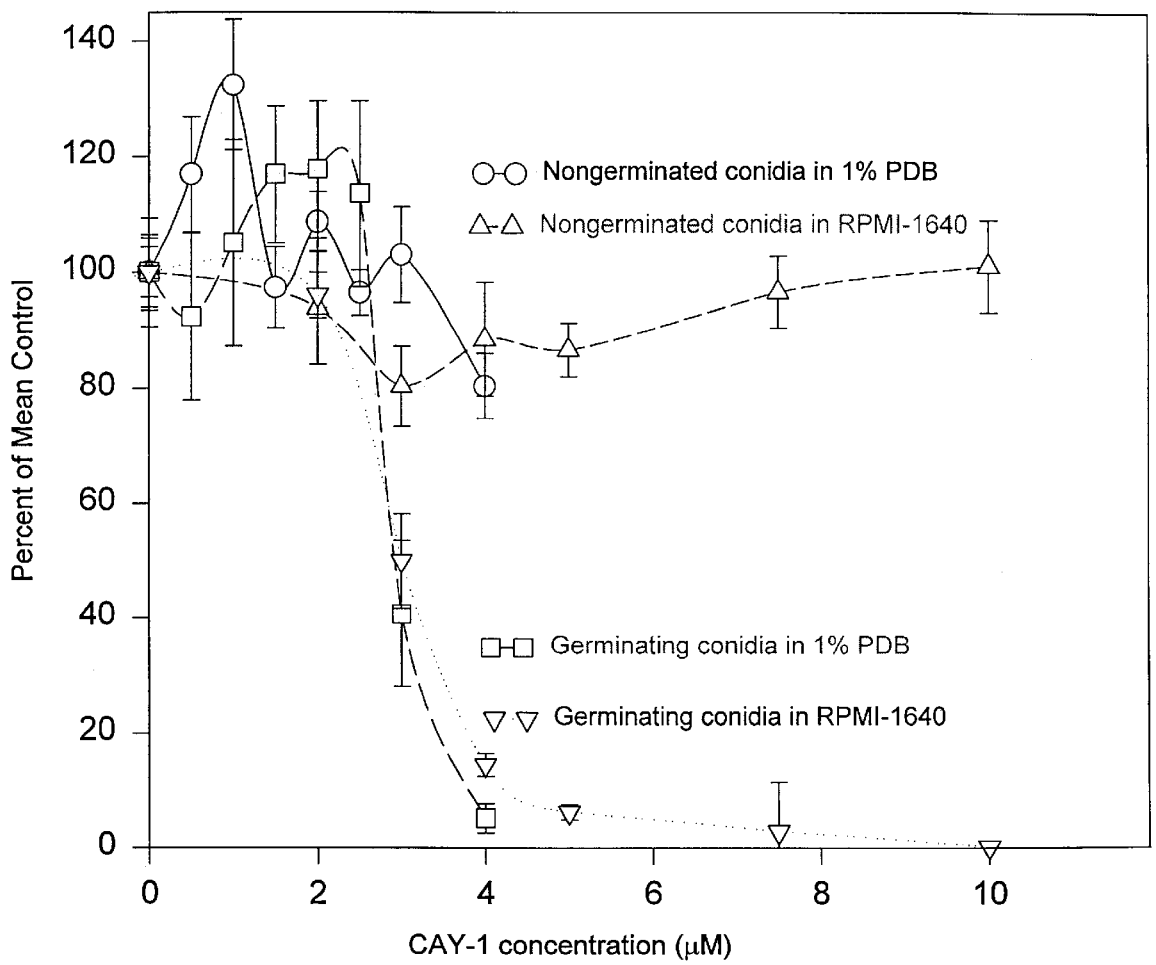
FIG. 3 shows the effect of CAY-1 on *Aspergillus fumigatus* as a function of CAY-1 concentration.

*A. fumigatus* (TABLE 2 & FIG. 3) was the filamentous fungus most sensitive to CAY-1 with the $LD_{95}$ attained at 4.0 µM (5.0 µg/ml). CAY-1 was lethal in both media with significant lethality achieved at 3.0 µM (3.7 µg/ml) in 1% (w/v) PDB (p=0.0002). However, a two-fold greater concentration of CAY-1, 10.0 µM (12.4 µg/ml), was required in RPMI-1640 to achieve statistically significant viability reduction (p=0.0002).

Figure 4:
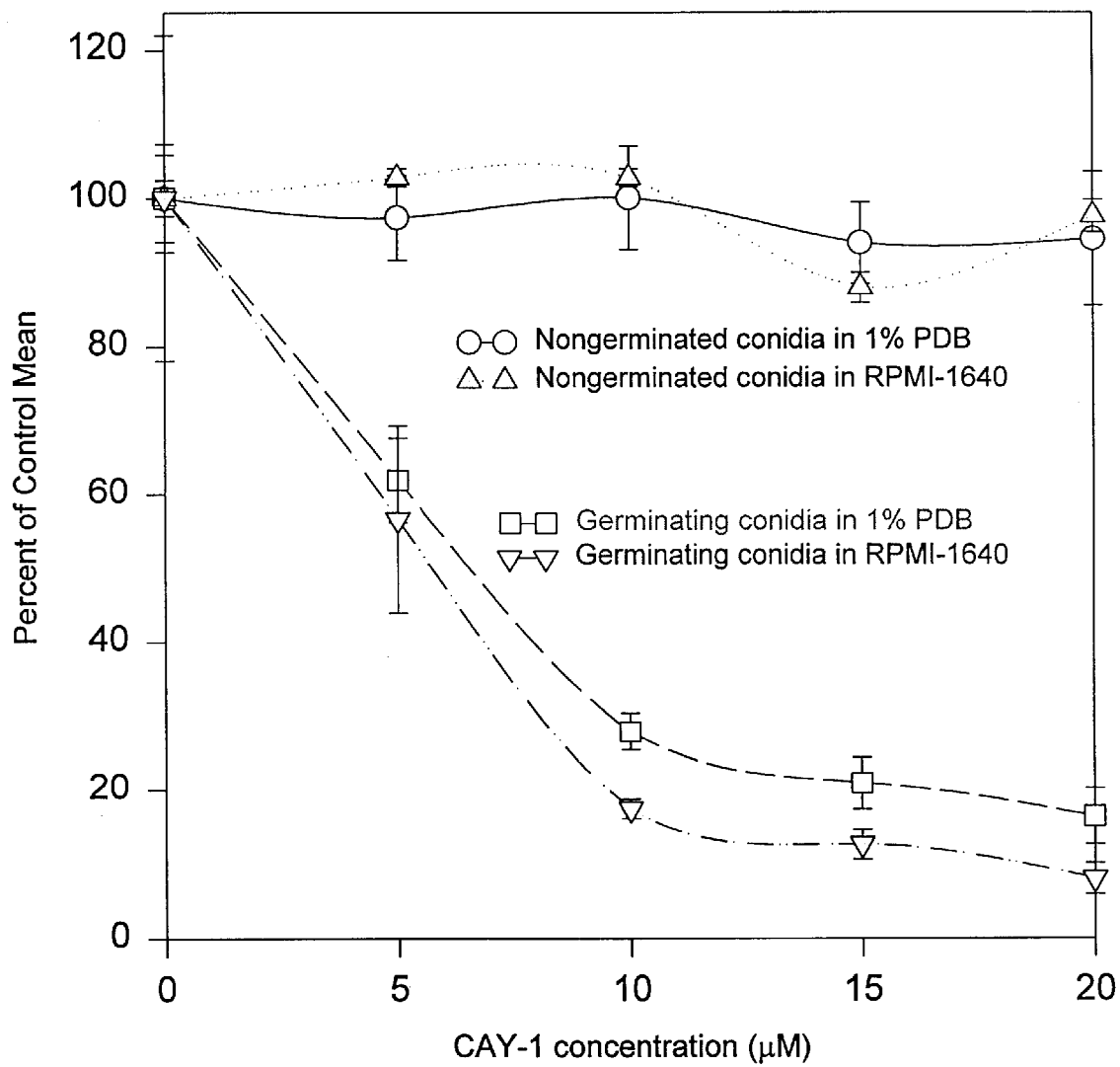
FIG. 4 shows the effect of CAY-1 on *Aspergillus parasiticus* as a function of CAY-1 concentration.

*A. parasiticus* was only slightly more resistant than *A. flavus* and *A. fumigatus* to CAY-1 (TABLE 3 & FIG. 4). CAY-1 significantly reduced the viability of the germinating conidia of *A. parasiticus* in 1% (w/v) PDB at 5 µM (6.2 µg/ml; p=0.001). As with *A. fumigatus*, a two-fold greater concentration of CAY-1 was required to obtain significant viability reduction in RPMI-1640 at 10.0 µM (12.4 µg/ml) with p=0.0002, than in 1% (w/v) PBD. A 92% viability reduction was achieved at 20.0 µM (24.8 µg/ml) in RPMI-1640 and a 85% viability reduction obtained in 1% (w/v) PDB at this concentration.

Figure 5:
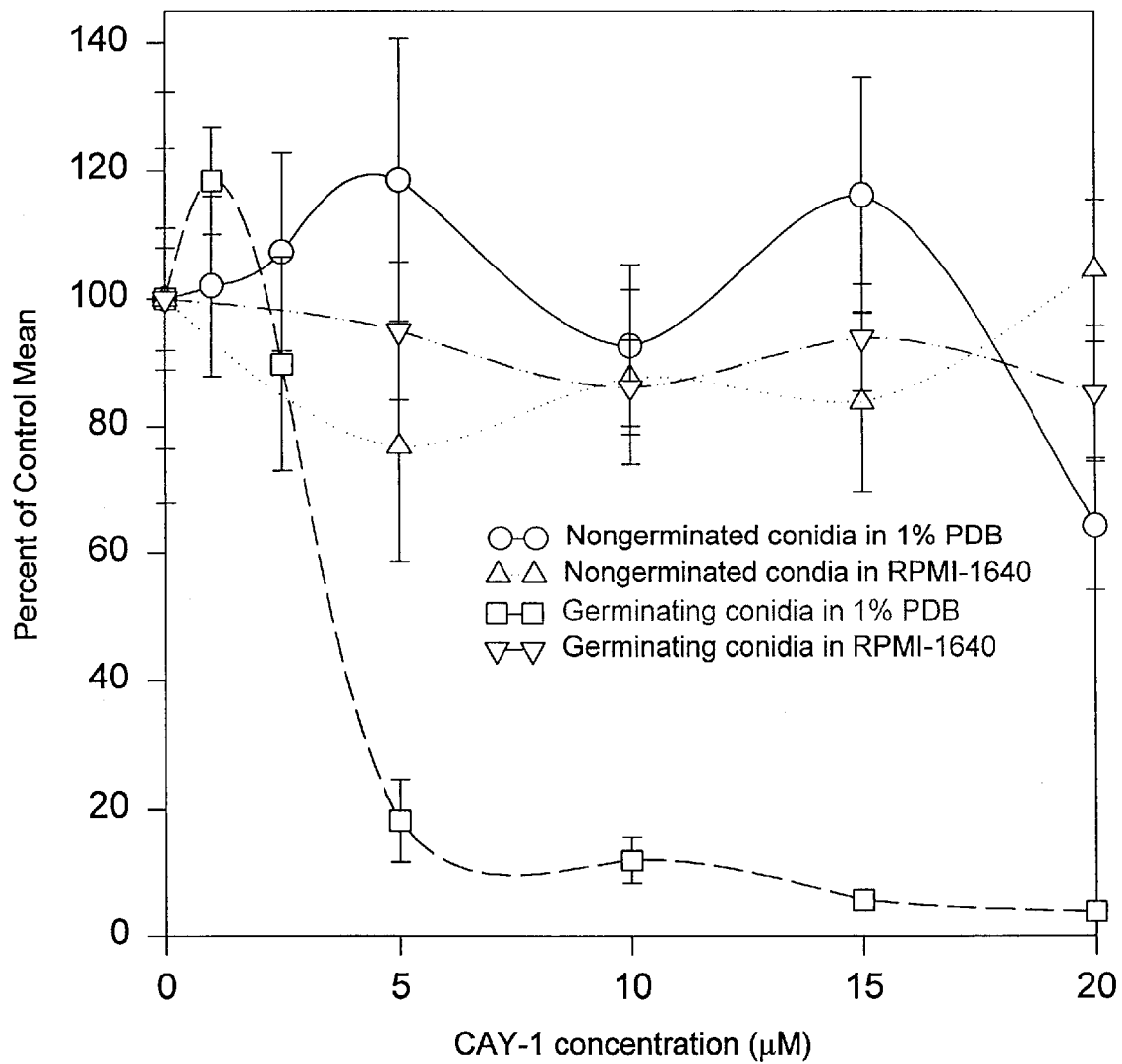
FIG. 5 shows the effect of CAY-1 on *Aspergillus niger* as a function of CAY-1 concentration.

The effect of media was most prominent in the assays with *A. niger* (TABLE 4 & FIG. 5). CAY-1 was only lethal to the germinating conidia of *A. niger* in 1% (w/v) PDB and no effect was observed in RPMI-1640. Significant lethality was obtained at 5.0 µM (6.2 µg/ml; p=0.0001) while $LD_{95}$, was reached at 15.0 µM (18.6 µg/ml) In contrast to results with germinating conidia, the viability of nongerminated conidia of the tested filamentous fungi were not affected by CAY-1 in either test medium. CAY-1 also was not active against the nongerminated and the germinating conidia of *F. oxysporum*.

2. *Candida albicans*. The effect of CAY-1 on *C. albicans* viability was determined by the NCCLS methods (National Committee for Clinical Laboratory Standards, Wayne, Pa., 1997. Reference method for broth dilution antifungal susceptibility testing of yeasts. Approved standard M-27A, herein incorporated by reference).

CAY-1 inhibited the growth of *C. albicans*. The $IC_{50}$ and $IC_{90}$ was determined to be 3.1 μM (3.8 μg/ml) and 6.2 μM (7.7 μg/ml), respectively.

3. *Pneumocystis carinii*. The effect of CAY-1 on *Pneumocystis carinii* was determined as described previously [Cushion et al., *Antimicrob. Agents Chemother.*, 1997, 41:379–384, herein incorporated by reference]. This assay is based on an ATP-driven bioluminescent reaction and was used to determine the concentration of CAY-1 which decreased the *P. carinii* ATP pools.

Figure 6:
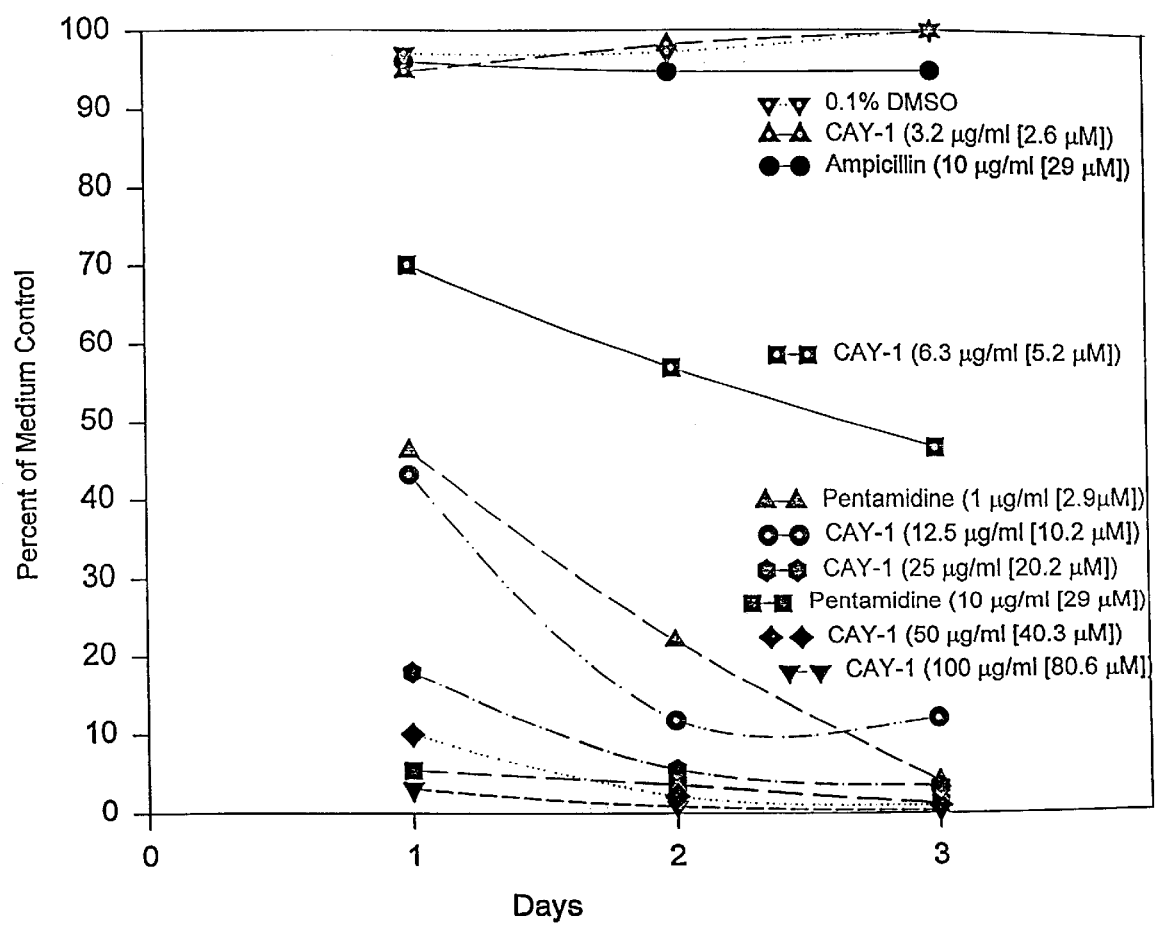
FIG. 6 shows the effect of CAY-1 on *Pneumocystis carinii* viability with time at various CAY-1 concentrations.

CAY-1 was lethal to *P. carinii* beginning at 5 μM (TABLE 5 & FIG. 6). Beginning on day 2, concentrations of as low as 12.5 μg/ml (10.0 μM) killed 34.6% and greater of the *P. carinii*. By day 3, 93% of the *P. carinii* cells were killed at a concentration of 50 μg/ml (40.3 μM). The $IC_{50}$ was determined to be 11.75 μg/ml (9.5 μM). CAY-1 at 25 and 50 μg/ml (20.2 and 40.3 μM, respectively) was as, or more effective, than pentamidine (10 μg/ml; 29 μM).

4. Time course study. The effect of time and concentration on the activity of CAY-1 was determined against the germinating conidia of *A. flavus* in 1% (w/v) PBD. Bioassays were performed twice as described above (n=8).

Figure 7:
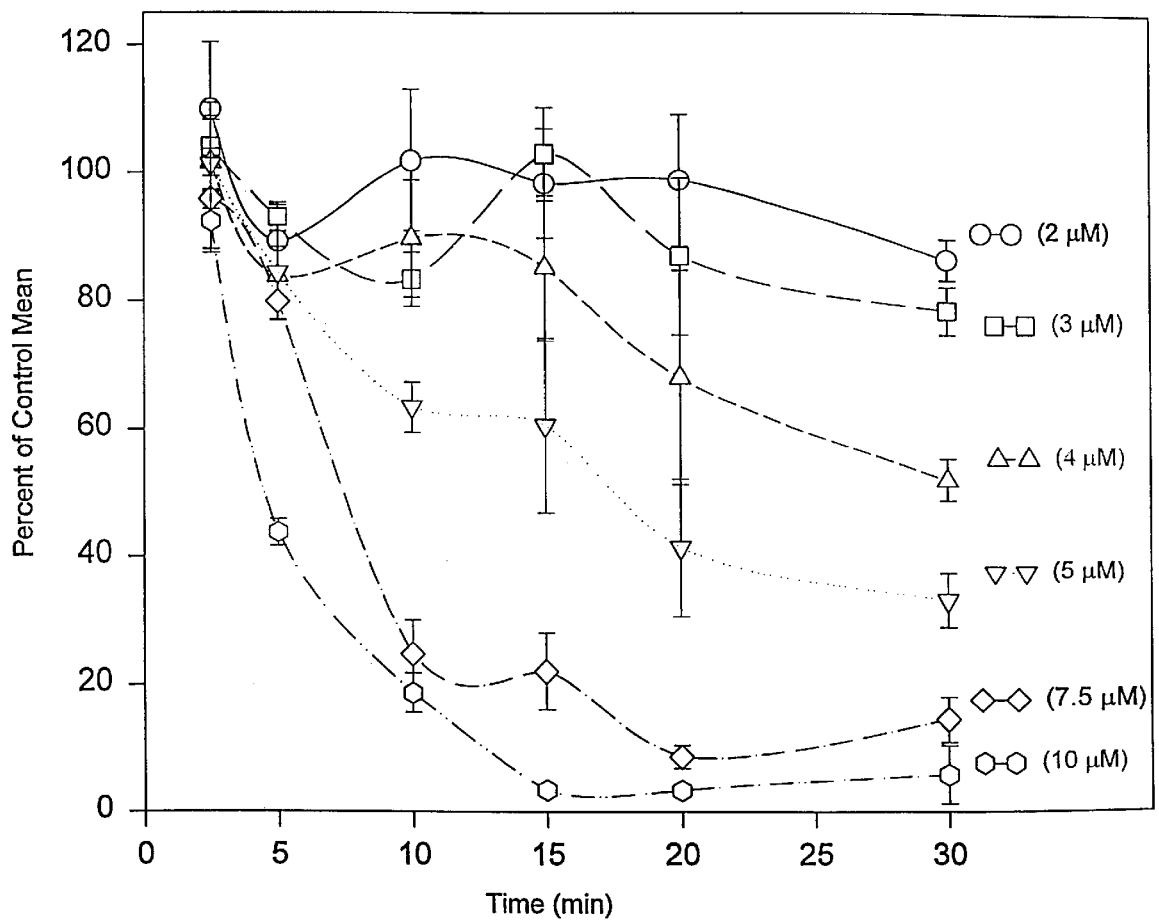
FIG. 7 shows the effect of CAY-1 concentration and time on germinating conidia of *Aspergillus flavus*.

CAY-1 activity showed dose and time dependency against the germinating conidia of *A. flavus* (TABLE 6 & FIG. 7). By 5 minutes post-incubation, significant lethality was observed at concentrations as low as 7.5 μM (9.3 μg/ml) with p=0.0072 at this concentration. At 10 minutes post-incubation, the concentration required for significant activity was reduced to 5.0 μM (6.2 μg/ml) with p=0.0001. Results indicate that $LD_{95}$ was achieved with 10 μM (12.4 μg/ml) by 15 minutes post-incubation.

5. Bacteria. CAY-1 lethality to *Escherichia coli* ATCC 8739, *Enterobacter agglomerans* ATCC 27996, *Bacillus subtilis* ATCC 6051 and *Staphylococcus aureus* ATCC 12600 was determined by methods described earlier (De Lucca et al., *Mol. cell Biochem.*, 1995, 151:141–148). Briefly, 24 hr bacterial cultures were washed and resuspended in 0.1 M PBS, pH 7.2, amended with 0.15 mM $MgCl_2$ and 0.5 mM $CaCl_2$ and adjusted to 80% transmittance (approximately $10^8$ cells/ml) at 590 nm. Bacterial suspensions were mixed with PBS and CAY-1 (final concentrations: 0, 0.5, 1, 2, 4, 8, 10 μM) in sterile 96-well plates (Nunc, Roskilde, Denmark) and incubated (37° C., 24 hrs). Bioassays were performed twice for each bacteria (n=8).

CAY-1 was not effective against any of the bacteria tested.

Statistical analyses. ANOVA analyses on ranks for non-parametric data were performed for the bioassays described in this example. Bonferroni's method was employed to determine which treatment groups were significantly different from the respective controls.

EXAMPLE 3

Mammalian Cytotoxicity Assays.

1. HeLa cells. Human epitheloid cervical carcinoma cells (ATCC2.2CCL) were grown in MEM media (Mediatech), supplemented with fetal bovine sera and penicillin (De Lucca et al., *Antimicrob. Agents Chemother.*, 1999, 43:371–373). The cells were rinsed with PBS and harvested using trypsin. Cell count was determined manually using trypan blue and cells were diluted to a final concentration of $2.5 \times 10^5$ CFU (Colony Forming Units)/ml. Aliquots of 100 μl were dispensed per well into a 96-well plate. Cells were incubated overnight (18–24 hours) at 37° C. in a humidified 5% (v/v) $CO_2$ environment. Neutral red dye solution was then added to each well culture and re-incubated for 3 hours. Two-fold serial dilutions of CAY-1 were prepared and aliquoted to final concentrations of 5, 10, 20, 30, and 60 μM (6, 12, 25, 37 and 74 μg/ml, respectively). Negative controls without CAY-1 were included. Cells were exposed to the saponin for 1 hour. Supernatants from each well were transferred into another 96-well plate. The remaining cells were lysed using a 2% Triton solution. Glacial acetic acid was then added to supernatants and lysates, and absorbance was read at A540.

Figure 8:
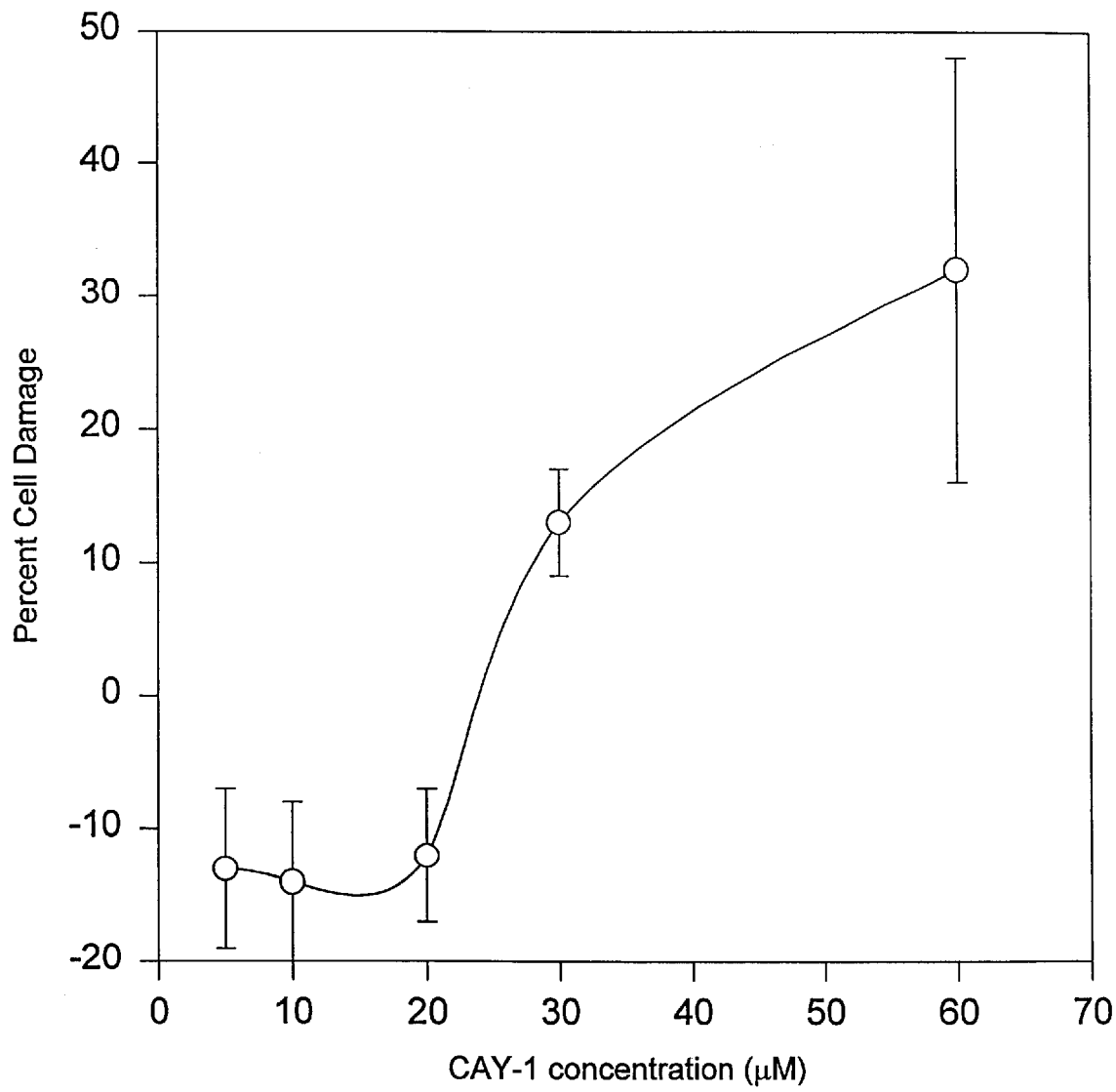
FIG. 8 shows the effect of CAY-2 on HeLa cells as a function of concentration.

CAY-1 demonstrated no cytotoxicity in HeLa cells until concentrations of 30 μM (37 μg/ml) were attained (FIG. 8). Approximately, 13% and 32% of the HeLa cells were damaged at concentrations of 30 μM (37 μg/ml) and 60 μμM (74 μg/ml), respectively.

2. A549 lung carcinoma cells. Toxicity of CAY-1 was tested by exposing the cells to CAY-1 for 24, 48, and 72 hrs. Antimycin A was used as a positive control. Viability was assessed by measurement of the ATP content in duplicate wells with luciferin-luciferase monitoring reagent [Cushion et al., *Antimicrob. Agents Chemother.*, 1997, 41:379–384].

There was no toxicity for A549 cells at 8 μM (10 μg/ml) of CAY-1 through day 3, though the highest dose, 80 μM (100 μg/ml) was highly lethal for the lung cells (FIG. 9).

TABLE 1

CAY-1 activity against nongerminated and germinating conidia of *Aspergillus flavus* in 1% potato dextrose broth and RPMI-1640[a]

| CAY-1 conc. (μM) | Mean No. of Colonies | S.E. | Percent of Mean Control | Percent of Control S.E. | p-value[b] |
|---|---|---|---|---|---|
| Nongerminated conidia of *A. flavus* in 1% potato dextrose broth. | | | | | |
| 0.0 | 53.5 | 3.9 | 100.0 | 7.3 | — |
| 2.0 | 54.4 | 2.8 | 101.7 | 5.2 | N/S |
| 3.0 | 54.8 | 2.4 | 102.4 | 4.5 | N/S |
| 4.0 | 55.2 | 2.3 | 103.2 | 4.3 | N/S |
| 5.0 | 55.7 | 2.2 | 104.1 | 4.1 | N/S |
| 7.5 | 56.9 | 3.1 | 106.4 | 5.8 | N/S |
| 10.0 | 58.0 | 4.5 | 108.4 | 8.4 | N/S |
| Germinating conidia of *A. flavus* in 1% potato dextrose broth. | | | | | |
| 0.0 | 155.2 | 5.4 | 100.0 | 3.5 | — |
| 2.0 | 139.8 | 3.8 | 90.1 | 2.4 | N/S |
| 3.0 | 115.4 | 4.1 | 74.4 | 2.6 | N/S |
| 4.0 | 84.1 | 3.7 | 54.2 | 2.4 | N/S |
| 5.0 | 54.2 | 4.7 | 34.9 | 3.0 | 0.0578 |
| 7.5 | 17.1 | 3.9 | 11.0 | 2.5 | 0.0026 |
| 10.0 | 13.1 | 4.9 | 8.4 | 3.2 | 0.0008 |
| Nongerminated conidia of *A. flavus* in RPMI-1640. | | | | | |
| 0.0 | 60.5 | 8.6 | 100.0 | 14.2 | — |
| 1.0 | 53.6 | 7.7 | 88.6 | 12.7 | N/S |
| 2.5 | 55.8 | 6.3 | 92.2 | 10.4 | N/S |
| 5.0 | 55.5 | 7.0 | 91.7 | 11.6 | N/S |
| 7.5 | 54.9 | 8.2 | 90.7 | 13.6 | N/S |
| 10.0 | 60.0 | 9.9 | 99.2 | 16.4 | N/S |
| Germinating conidia of *A. flavus* in RPMI-1640. | | | | | |
| 0.0 | 39.9 | 4.3 | 100.0 | 10.8 | — |
| 1.0 | 52.6 | 10.5 | 131.8 | 26.9 | N/S |
| 2.5 | 57.8 | 8.4 | 144.8 | 21.1 | N/S |
| 5.0 | 25.1 | 3.1 | 62.9 | 7.8 | N/S |
| 7.5 | 5.6 | 1.0 | 14.0 | 2.5 | 0.0187 |
| 10.0 | 3.6 | 1.3 | 9.0 | 3.3 | 0.0184 |

[a]Duplicate runs. (n = 8).
[b]N/S = Not statistically different from respective control. A 5% level of significance was used.

TABLE 2

CAY-1 activity against nongerminated and germinating conidia of *Aspergillus fumigatus* in 1% potato dextrose broth and RPMI-1640[a]

| CAY-1 conc. ($\mu$M) | Mean No. of Colonies | S.E. | Percent of Mean Control | Percent of Control S.E. | p-value[b] |
|---|---|---|---|---|---|
| Nongerminated conidia of *A. fumigatus* in 1% potato dextrose broth. | | | | | |
| 0.0 | 61.1 | 4.0 | 100.0 | 6.5 | — |
| 2.0 | 57.4 | 5.9 | 93.9 | 9.7 | N/S |
| 3.0 | 49.1 | 4.2 | 80.4 | 6.9 | N/S |
| 4.0 | 54.1 | 5.3 | 88.5 | 9.8 | N/S |
| 5.0 | 53.0 | 2.8 | 86.7 | 4.6 | N/S |
| 7.5 | 59.0 | 3.7 | 96.6 | 6.1 | N/S |
| 10.0 | 61.8 | 4.8 | 101.1 | 7.9 | N/S |
| Germinating conidia of *A. fumigatus* in 1% potato dextrose broth. | | | | | |
| 0.0 | 45.9 | 2.7 | 100.0 | 5.9 | — |
| 2.0 | 44.1 | 1.8 | 96.1 | 3.9 | N/S |
| 3.0 | 22.9 | 3.8 | 49.9 | 8.3 | 0.0002 |
| 4.0 | 6.6 | 0.9 | 14.4 | 2.0 | <0.0001 |
| 5.0 | 2.8 | 0.6 | 6.1 | 1.3 | <0.0001 |
| 7.5 | 1.3 | 0.4 | 2.8 | 0.9 | <0.0001 |
| 10.0 | 0.1 | 0.1 | 0.2 | 0.2 | <0.0001 |
| Nongerminated conidia of *A. fumigatus* in RPMI-1640. | | | | | |
| 0.0 | 23.1 | 1.0 | 100.0 | 4.3 | — |
| 0.5 | 27.0 | 2.3 | 116.9 | 10.0 | N/S |
| 1.0 | 30.6 | 2.6 | 132.5 | 11.5 | N/S |
| 1.5 | 22.5 | 1.6 | 97.4 | 6.9 | N/S |
| 2.0 | 25.1 | 1.2 | 108.7 | 5.2 | N/S |
| 2.5 | 22.3 | 0.9 | 96.5 | 3.9 | N/S |
| 3.0 | 23.8 | 1.9 | 103.0 | 5.6 | N/S |
| Germinating conidia of *A. fumigatus* in RPMI-1640. | | | | | |
| 0.0 | 11.8 | 1.1 | 100.0 | 9.3 | — |
| 0.5 | 10.9 | 1.7 | 92.4 | 14.4 | N/S |
| 1.0 | 12.4 | 2.1 | 105.1 | 17.8 | N/S |
| 1.5 | 13.8 | 1.4 | 116.9 | 11.9 | N/S |
| 2.0 | 13.9 | 1.4 | 117.8 | 11.9 | N/S |
| 2.5 | 13.5 | 1.9 | 113.6 | 16.1 | N/S |
| 3.0 | 4.8 | 1.5 | 40.7 | 12.7 | 0.0021 |
| 4.0 | 0.6 | 0.3 | 5.1 | 2.5 | 0.0001 |

[a]Duplicate runs. (n = 8).
[b]N/S = Not statistically different from respective control. A 5% level of significance was used.

TABLE 3

CAY-1 activity against nongerminated and germinating conidia of *Aspergillus parasiticus* in 1% potato dextrose broth and RPMI-1640[a]

| CAY-1 conc. ($\mu$M) | Mean No. of Colonies | S.E. | Percent of Mean Control | Percent of Control S.E. | p-value[b] |
|---|---|---|---|---|---|
| Nongerminated conidia of *A. parasiticus* in 1% potato dextrose broth. | | | | | |
| 0.0 | 54.6 | 3.2 | 100.0 | 5.9 | — |
| 5.0 | 53.1 | 3.1 | 97.3 | 5.7 | N/S |
| 10.0 | 54.6 | 3.8 | 100.0 | 7.0 | N/S |
| 15.0 | 51.3 | 3.0 | 93.9 | 5.5 | N/S |
| 20.0 | 51.9 | 4.9 | 94.5 | 9.0 | N/S |
| Germinating conidia of *A. parasiticus* in 1% potato dextrose broth. | | | | | |
| 0.0 | 154.4 | 11.2 | 100.0 | 7.3 | — |
| 5.0 | 95.5 | 8.8 | 61.9 | 5.7 | 0.0001 |
| 10.0 | 43.3 | 3.8 | 28.0 | 2.5 | 0.0001 |
| 15.0 | 32.5 | 5.4 | 21.0 | 3.5 | 0.0001 |
| 20.0 | 25.5 | 5.9 | 16.5 | 3.8 | 0.0001 |
| Nongerminated conidia of *A. parasiticus* in RPMI-1640. | | | | | |
| 0.0 | 41.4 | 1.0 | 100.0 | 2.4 | — |
| 5.0 | 42.5 | 0.5 | 102.7 | 1.2 | N/S |
| 10.0 | 42.5 | 1.2 | 102.7 | 1.2 | N/S |
| 15.0 | 36.4 | 0.8 | 87.9 | 2.0 | N/S |
| 20.0 | 40.4 | 0.9 | 97.6 | 2.2 | N/S |
| Germinated conidia of *A. parasiticus* in RPMI-1640. | | | | | |
| 0.0 | 70.8 | 15.5 | 100.0 | 21.9 | — |
| 5.0 | 40.1 | 9.0 | 56.6 | 12.7 | NJS |
| 10.0 | 12.4 | 0.9 | 17.5 | 1.3 | 0.0002 |
| 15.0 | 9.0 | 1.4 | 12.7 | 2.0 | 0.0002 |
| 20.0 | 5.7 | 1.5 | 8.1 | 2.1 | 0.0003 |

[a]Duplicate runs. (n = 8).
[b]N/S = Not statistically different from respective control. A 5% level of significance was used.

TABLE 4

CAY-1 activity against nongerminated and germinating conidia of *Aspergillus niger* in 1% potato dextrose broth and RPMI-1640[a]

| CAY-1 conc. ($\mu$M) | Mean No. of Colonies | S.E. | Percent of Mean Control | Percent of Control S.E. | p-value[b] |
|---|---|---|---|---|---|
| Nongerminated conidia of *A. niger* in 1% potato dextrose broth. | | | | | |
| 0.0 | 35.7 | 8.4 | 100.0 | 23.5 | — |
| 1.0 | 36.5 | 5.0 | 102.2 | 14.0 | N/S |
| 2.5 | 34.5 | 5.7 | 96.6 | 16.0 | N/S |
| 5.0 | 42.3 | 7.9 | 118.5 | 22.1 | N/S |
| 10.0 | 33.1 | 4.5 | 92.7 | 12.6 | N/S |
| 15.0 | 41.5 | 6.6 | 116.0 | 18.5 | N/S |
| 20.0 | 23.0 | 3.6 | 64.4 | 10.1 | N/S |
| Germinating conidia of *A. niger* in 1% potato dextrose broth. | | | | | |
| 0.0 | 51.0 | 5.6 | 100.0 | 11.0 | — |
| 1.0 | 60.4 | 4.3 | 118.4 | 8.4 | N/S |
| 2.5 | 45.8 | 8.6 | 89.8 | 16.7 | N/S |
| 5.0 | 9.3 | 3.3 | 18.2 | 6.5 | 0.0001 |
| 10.0 | 6.1 | 1.9 | 12.0 | 3.7 | 0.0001 |
| 15.0 | 2.9 | 0.8 | 5.7 | 1.6 | 0.0002 |
| 20.0 | 2.0 | 0.7 | 3.9 | 1.4 | 0.0002 |
| Nongerminated conidia of *A. niger* in RPMI-1640. | | | | | |
| 0.0 | 48.8 | 15.8 | 100.0 | 32.3 | — |
| 5.0 | 37.5 | 8.9 | 76.8 | 18.2 | N/S |
| 10.0 | 42.8 | 6.7 | 87.7 | 13.7 | N/S |
| 15.0 | 40.9 | 6.9 | 83.8 | 14.1 | N/S |
| 20.0 | 51.0 | 5.4 | 104.5 | 11.1 | N/S |
| Germinated conidia of *A. niger* in RPMI-1640. | | | | | |
| 0.0 | 52.8 | 4.2 | 100.0 | 8.0 | — |
| 5.0 | 50.1 | 5.7 | 94.9 | 10.8 | N/S |
| 10.0 | 45.5 | 3.9 | 86.2 | 7.4 | N/S |
| 15.0 | 49.6 | 4.4 | 93.9 | 8.3 | N/S |
| 20.0 | 45.1 | 5.5 | 85.4 | 10.4 | N/S |

[a]Duplicate runs. (n = 8).
[b]N/S = Not statistically different from respective control. A 5% level of significance was used.

TABLE 5

Effect of CAY-1 on *Pneumocystis carinii* viability

| | Percent of Control Mean | | |
|---|---|---|---|
| Compound Concentration | Day 1 | Day 2 | Day 3 |
| Ampicillin (10 $\mu$g/ml; 29 $\mu$M)[1] | 96.0 | 94.7 | 94.8 |
| Pentamidine (10 $\mu$g/ml; 29 $\mu$M)[2] | 5.4 | 3.5 | 1.2 |

TABLE 5-continued

Effect of CAY-1 on *Pneumocystis carinii* viability

| Compound Concentration | Percent of Control Mean | | |
|---|---|---|---|
| | Day 1 | Day 2 | Day 3 |
| Pentamidine (1 μg/ml; 2.9 μM)[2] | 46.2 | 22.0 | 3.9 |
| CAY-1 (100 μg/ml; 80 μM) | 3.1 | 0.9 | 0.3 |
| CAY-1 (50 μg/ml; 40 μM) | 10.0 | 2.2 | 1.0 |
| CAY-1 (25 μg/ml; 20 μM) | 18.0 | 5.5 | 3.3 |
| CAY-1 (12.5 μg/ml; 10 μM) | 43.1 | 11.8 | 12.1 |
| CAY-1 (6.3 μg/ml; 5 μM) | 70.1 | 56.9 | 46.6 |
| CAY-1 (3.2 μg/ml; 2.5 μM) | 94.7 | 98.2 | 99.8 |
| DMSO (0.1%) | 97.1 | 97.3 | 100.0 |

[1] Negative control
[2] Positive control

TABLE 6

Effect of incubation time and dose on the fungicidal activity of CAY-1 for the germinating conidia of *Aspergillus flavus* in 1% potato dextrose broth[a]

| CAY-1 conc. (μM) | Mean No. of Colonies | S.E. | Percent of Mean Control | Percent of Control S.E. | p-value[b] |
|---|---|---|---|---|---|
| *Time: 2.5 min post incubation.* | | | | | |
| 0.0 | 167.8 | 13.4 | 100.0 | 8.0 | — |
| 2.0 | 184.4 | 17.7 | 109.9 | 10.5 | N/S |
| 3.0 | 174.3 | 11.7 | 103.9 | 7.0 | N/S |
| 4.0 | 170.5 | 12.2 | 101.6 | 7.3 | N/S |
| 5.0 | 170.0 | 11.7 | 101.3 | 7.0 | N/S |
| 7.5 | 160.8 | 13.1 | 95.8 | 7.8 | N/S |
| 10.0 | 154.8 | 8.3 | 92.3 | 4.9 | N/S |
| *Time: 5.0 min post incubation.* | | | | | |
| 0.0 | 204.4 | 11.6 | 100.0 | 5.7 | — |
| 2.0 | 182.3 | 11.6 | 89.2 | 5.7 | N/S |
| 3.0 | 190.1 | 4.6 | 93.0 | 2.3 | N/S |
| 4.0 | 171.3 | 9.2 | 83.8 | 4.5 | N/S |
| 5.0 | 172.4 | 15.0 | 84.3 | 7.3 | N/S |
| 7.5 | 163.3 | 6.1 | 79.9 | 3.0 | 0.0072 |
| 10.0 | 89.8 | 4.4 | 43.8 | 2.2 | <0.0001 |
| *Time: 10.0 min post incubation.* | | | | | |
| 0.0 | 133.0 | 10.7 | 100.0 | 8.0 | — |
| 2.0 | 135.5 | 14.7 | 101.9 | 11.1 | N/S |
| 3.0 | 110.8 | 5.6 | 83.3 | 4.2 | N/S |
| 4.0 | 119.3 | 12.1 | 89.7 | 9.1 | N/S |
| 5.0 | 84.3 | 5.2 | 63.4 | 3.9 | 0.0011 |
| 7.5 | 32.8 | 7.0 | 24.7 | 5.3 | <0.0001 |
| 10.0 | 24.9 | 4.1 | 18.7 | 3.1 | <0.0001 |
| *Time: 15 min post incubation.* | | | | | |
| 0.0 | 128.0 | 5.1 | 100.0 | 4.0 | — |
| 2.0 | 126.0 | 11.0 | 98.4 | 8.6 | N/S |
| 3.0 | 131.9 | 9.4 | 103.0 | 7.3 | N/S |
| 4.0 | 109.1 | 14.5 | 85.2 | 11.3 | N/S |
| 5.0 | 77.6 | 17.5 | 60.6 | 13.7 | 0.0152 |
| 7.5 | 28.1 | 7.7 | 22.0 | 6.0 | <0.0001 |
| 10.0 | 4.4 | 0.7 | 3.4 | 0.5 | <0.0001 |
| *Time: 20 min post inoculation.* | | | | | |
| 0.0 | 229.9 | 27.8 | 100.0 | 12.1 | — |
| 2.0 | 227.4 | 23.8 | 98.9 | 10.4 | N/S |
| 3.0 | 200.0 | 28.1 | 87.0 | 12.2 | N/S |
| 4.0 | 156.4 | 38.5 | 68.0 | 16.7 | N/S |
| 5.0 | 95.5 | 24.8 | 41.5 | 10.8 | 0.0028 |
| 7.5 | 19.8 | 4.2 | 8.6 | 1.8 | <0.0001 |
| 10.0 | 7.6 | 2.3 | 3.3 | 1.0 | <0.0001 |
| *Time: 30 min post incubation.* | | | | | |
| 0.0 | 155.2 | 5.4 | 100.0 | 3.5 | — |
| 2.0 | 139.8 | 3.8 | 90.1 | 2.4 | N/S |
| 3.0 | 115.4 | 4.1 | 74.4 | 2.6 | N/S |
| 4.0 | 84.1 | 3.7 | 54.2 | 2.4 | N/S |
| 5.0 | 54.2 | 4.7 | 34.9 | 3.0 | 0.0578 |
| 7.5 | 17.1 | 3.9 | 11.0 | 2.5 | 0.0026 |
| 10.0 | 13.1 | 4.9 | 8.4 | 3.2 | 0.0008 |

[a] Two separate assays performed per time and concentration set (n = 8).
[b] N/S = Not statistically different from respective control. A 5% level of significance was used.

We claim:

1. An isolated compound having the following formula:

2. An antifungal composition comprising:

(1) a compound having the following formula:

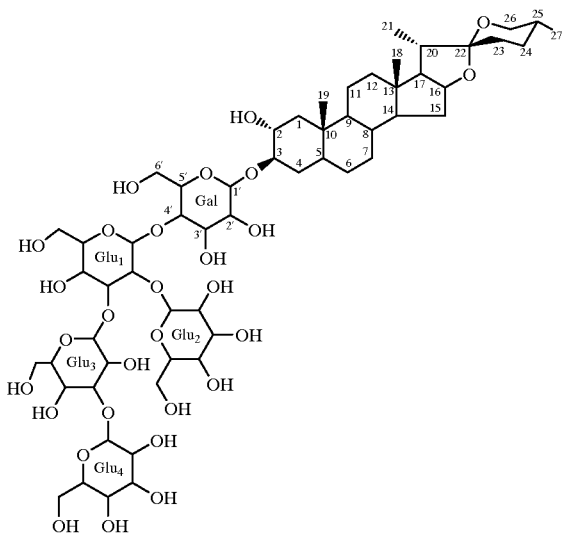

(2) a carrier or vehicle for said compound, wherein said compound is present in an amount effective to inhibit the growth of a fungal organism.

3. The composition of claim 2, wherein said fungal organism is a filamentous fungus.

4. The antifungal composition of claim 2, wherein said effective amount is at least about 3 μM.

5. A method for inhibiting the growth of a fungal organism comprising the step of applying to a substrate susceptible to inoculation with said fungal organism a compound having the following formula:

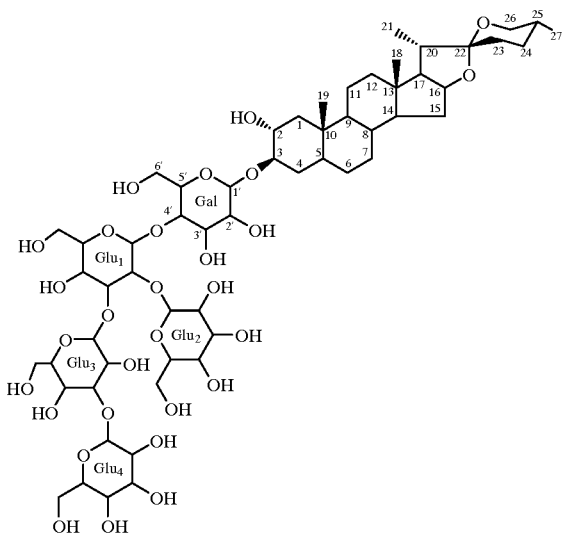

wherein said compound is in an amount effective to inhibit said growth.

6. The method of claim 5, wherein said fungal organism is a filamentous fungus.

7. The method of claim 5, wherein said fungal organism is an aflatoxin-producing organism.

8. The method of claim 5, wherein said fungal organism is selected from the group consisting of *Aspergillus flavus*, *Aspergillus fumigatus*, *Aspergillus parasiticus*, and *Aspergillus niger*.

9. The method of claim 5, wherein said substrate is a plant or plant part.

10. The method of claim 5, wherein said substrate is a food or feed material.

11. The method of claim 5, wherein said substrate is a seed.

12. The method of claim 5, wherein said fungal organism is a human mycosis-inducing fungal pathogen.

13. The method of claim 12, wherein said fungal organism is selected from the group consisting of *Pneumocystis carnii* and *Candida albicans*.

14. The method of claim 12, wherein said substrate is a human or animal.

15. The method of claim 12, wherein said substrate is a wound.

* * * * *